United States Patent
Aradi et al.

(10) Patent No.: US 6,403,843 B1
(45) Date of Patent: Jun. 11, 2002

(54) PROCESS FOR THE PREPARATION OF 1-(3,4-DIMETHOXYPHENYL)ETHANOL

(75) Inventors: Matyas Aradi; Geza Arvai; Bela Bertok, all of Budapest; Zsuzsanna Kuruczne Ribai, Erd; Erzsebet Szalay, Budapest; Istvan Szekely, Dunakeszi, all of (HU)

(73) Assignee: Agro-Chemie, Budapest (HU)

( * ) Notice: Subject to any disclaimer, the term of this patent is extended or adjusted under 35 U.S.C. 154(b) by 0 days.

(21) Appl. No.: 09/445,508

(22) PCT Filed: Jul. 28, 1998

(86) PCT No.: PCT/HU98/00072

§ 371 (c)(1),
(2), (4) Date: Mar. 29, 2000

(87) PCT Pub. No.: WO99/06343

PCT Pub. Date: Feb. 11, 1999

(30) Foreign Application Priority Data

Jul. 31, 1997 (HU) .............................. 9701335

(51) Int. Cl.$^7$ .............................. C07C 41/20

(52) U.S. Cl. .................................... 568/648

(58) Field of Search ........................ 568/648

(56) References Cited

PUBLICATIONS

A. Muller et al, "Ueber die Dimerisation des Isoeugenolmethylathers (Harzphenole I)." vol. 75, No. 6, Jun. 6, 1942, pp. 692–703.

A.G. Davies et al, Journal of the Chemical Society, 1957, pp. 3158–3161.

C.H. Ludwig et al, Journal of the American Chemical Society, vol. 86, Mar. 20, 1964, pp. 1186–1196.

B. Figadere et al, Journal of Organic Chemistry, vol. 59, No. 23, 1994, pp. 7138–7141.

*Primary Examiner*—Sreeni Padmanabhan
*Assistant Examiner*—Sikarl A. Witherspoon
(74) *Attorney, Agent, or Firm*—Birch, Stewart, Kolasch & Birch, LLP

(57) ABSTRACT

The subject of our invention is the process for the preparation of the 1-(3,4-dimethoxyphenyl)ethanol of formula (I), by the reduction of 3,4-dimethoxyacetophenone of formula (II), characterized in that the carbonyl group of the 3,4-dimethoxyacetophenone of formula (II) is reduced by 1 mol of hydrogen under the conditions of catalytic hydrogenation.

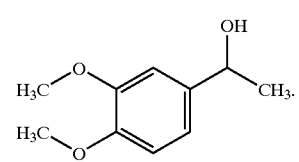

7 Claims, 1 Drawing Sheet

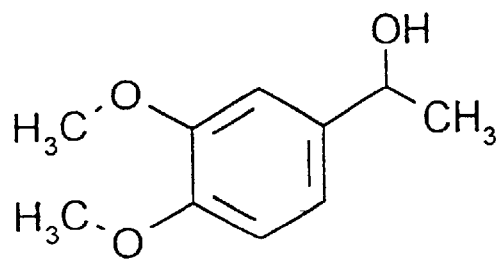
I.
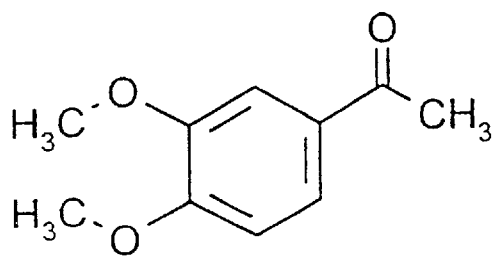
II.
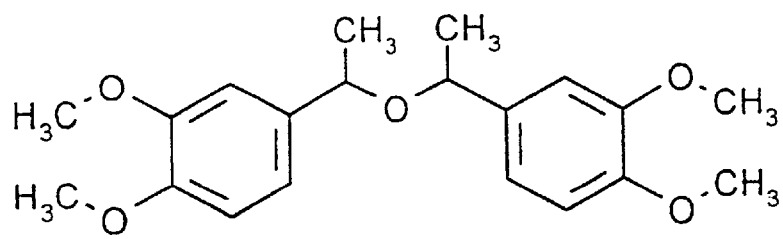
III.
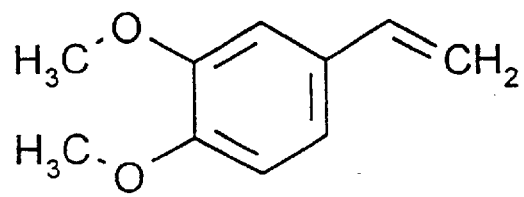
IV.
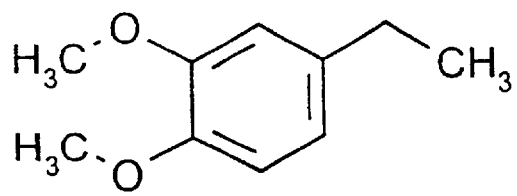
V.

PROCESS FOR THE PREPARATION OF 1-(3,4-DIMETHOXYPHENYL)ETHANOL

This application is the national phase under 35 U.S.C. §371 of PCT International Application No. PCT/HU98/00072 which has an International filing date of Jul. 28, 1998, which designated the United States of America.

The subject of the present invention is the heterogenous catalytic hydrogenation process, suitable for scaling up, for the synthesis of 1-(3,4-dimethoxyphenyl)ethanol (by other name α-methylveratryl alcohol) of formula I. by the reduction of 3,4-dimethoxyacetophenone of formula II.

The title compound is the starting material to a number of important compounds and there is a growing demand for it. Among others, it can favourably be used for the preparation of the insecticide synergists described in WO 97/19040 and Hungarian patent applications No 3318/95 and 0893/97. Therefore, elaboration of an economical technology was required. It was necessary that the crude product obtained in the process be of high purity and not require purification operations, like for instance distillation. The 1-phenylethanols substituted with methoxy groups are namely surprisingly sensitive compounds and they can be purified only with substantial losses. On the effect of heat during the distillation, and/or on the effect of traces of acids or bases the above compounds readily transform into the bis-phenylethyl ethers of formula III (Chem. Pharm. Bull. 31, 3024 (1983); J. Chem. Soc. 3158 (1957); J. Am. Chem. Soc. 70, 1895 (1948)), or via dehydration they can form the styrene derivative of formula IV. (J. Am. Chem. Soc. 106, 1361 (1984)).

In the literature there are two basic methods for the synthesis of 1-(3,4-dimethoxyphenyl)ethanol. According to the first method the compound is prepared by the reaction of 3,4-dimethoxybenzaldehyde and methylmagnesium iodide (Chem. Pharm. Bull. 31, 3024 (1983)); according to the second by the reduction of 3',4'-dimethoxyacetophenone (by other name acetoveratrone). The latter reduction can be performed by using sodium borohydride (Bull. Soc. Chim. France 1973 2667; J. Chem. Soc. Perkin 2 1994, 961; J. Am. Chem Soc. 86, 1186 (1964)), tributyltin hydride (J. Org. Chem. 59 7138 (1994)), sodium in ethanol (Arch. Pharm (Weinheim Ger.) 248, 139 (1910)), or aluminium isopropoxide (Ann. 1995, 677) in isopropanol. None of the above methods is suitable for large-scale technology, considering the costly reagents, the specific reaction conditions (eg. anhydrous solvents), the resulting waste materials, as well as the complicated work-up and purification procedures.

There is no reference in the literature for the heterogeneous catalytic hydrogenation of the acetoveratrone of formula II. This is surprising, since this route seems to be the most economical for the preparation of the compound of formula I, in an industrial scale.

Hydrogenation of the carbonyl group requires active catalyst. For the reduction of acetophenones catalysts as platinum metals (platinum, palladium, rhodium, ruthenium, iridium) (Ann. 1924, 276; J. Org. Chem. 24, 1885 (1959); Bull. Chem. Soc. Jpn. 34, 32 (1961)), nickel (J. Am. Chem Soc. 52, 4349 (1930); J. Org. Chem. 45, 1937, 1946 (1980)), Raney-nickel (J. Am. Chem. Soc. 70, 695 (1948); J. Chem. Soc. 3158 (1957); Ann. 714, 91 (1968); Bull. Soc. Chim. France 1972, 4324), or copper chromite (J. Am. Chem. Soc. 53, 1090 (1931)) may be used. The selectivity of these metals is, however, different. Rhodium catalyst is inclined to also saturate the ring, platinum, depending on the solvent and the pH, may cause hydrogenolysis, i.e the ethylbenzene by-product of formula V, will appear. For the catalytic hydrogenation of acetophenones the literature suggests the use of 10% palladium-on charcoal catalyst (Paul Rylander, Catalytic Hydrogenation in Organic Synthesis; p103, Academic Press, 1979).

Our first experiments verified that the known methods cannot directly be used. Hydrogenation of the acetoveratrone of formula II, following the procedure suggested by the literature, using 10% palladium-on charcoal catalyst, under normal conditions (25° C., 1 atm), in methanol as solvent, did not lead to homogeneous product.. Beside the expected 1-(3,4-dimethoxyphenyl)ethanol a high amount of ethylveratrole was also formed. The hydrogenation of the keto group and the hydrolysis of the C—O bond of the product proceeded simultaneously, at comparable rate, and in addition a considerable amount of 1-(3,4-dimethoxyphenyl)ethyl methyl ether by-product was also isolated. The electron-donating alkoxy groups activate the benzylic carbon atom to nucleofilic substitution, thus the latter in the given environment, for instance on the surface of the catalyst may react with a nucleophilic partner, in our case with the solvent, i.e. alcohol, but it may even react with the product of the reduction, i.e. with the α-methylveratryl alcohol. To all this is added the sensitivity of the desired α-methylveratryl alcohol of formula I, which makes the accomplishment of the process even more difficult, and which also explains why hydrogenation was not used for the preparation of that compound.

The growing demand for the compound in question, as well as the inexpensive implementation of catalytic hydrogenations, inspired us, despite the above difficulties, to work out a hydrogenation process which is exempt from the above disadvantages, ie. which results the desired compound of formula I in higher yield, higher purity and more economically than the previous methods.

Although rarely, nickel and Raney-nickel are also used for the hydrogenation of phenones, the reactions being carried out mainly in ethanolic or methanolic medium. According to the relevent literature a successful reaction requires rather drastic conditions (Paul Rylander, Catalytic Hydrogenation in Organic Synthesis, p83, Academic Press, 1979). As a concequence, one can expect in these reactions as well, the appearance of the appropriate 1-phenylethyl ethyl or methyl ether. The formation of this by-product can theoretically be exluded if aqueous medium or neutral catalyst is applied. Even though, no example can be find in the literature for hydrogenation of the given group of compounds in aqueous medium. The reason for that may be that the starting material and the product as well are expected to be rather insoluble in water, their solvation does not proceed, while the surface of the catalyst is deactivated, due to the polar solvate layer. (Paul Rylander, Catalytic Hydrogenation in Organic Synthesis, p83, Academic Press, 1979), all of these will cause the slowing-down of the reduction, and in the light of the above, the formation of by-products. To investigate this point, we calculated the partition ratio of acetoveratrone. To our surprise, a rather low value (calculated 1 gP≅1.22, K(octanol, water)≅16) was obtained. This means that the material has a weak, hydrophilic character and a suitable polarity. By increasing the temperature this value may further be ameliorated, which means that there was a chance that the reaction can proceed and the by-product formation can be suppressed. Carrying out the hydrogenation at a temperature higher than the melting point of the starting material (50° C.), suitable dispersity and solvation equlibrium may be ensured by vigourous stirring of the melt in the aqueous medium. Our expectations have been proven by our experiments. We investigated the hydrogenation of acetoveratrone at 20–80° C., by using neutral Raney-nickel catalyst. After 5–48 hours full transformation and the formation of homogeneous product was observed. If the reaction was performed at 50–80° C., under 6–10 bar hydrogen pressure, full conversion was achieved in much shorter time, depending on the intensity of the stirring (700–1250 l/min) the reaction accomplished in 3–7 hours. The product was obtained from the reaction mixture following evaporation under reduced pressure. Yields were in each case over 98%. As shown by analytical investigation (GC, HPLC, VRK) starting from a raw material of over 98% purity the assay for the product was higher than 97%. Total amuont of the unreacted starting material and the ethylveratrole by-product was as little as about 0.5%. The high purity of the product is well shown by the phenomenon, that on standing it crystallized, although previously this compound was only known as a viscous oil and no data for its melting point have been disclosed.

The subject of our invention, in accordance with the above, is a process for the preparation of 1-(3,4-dimethoxyphenyl)ethanol of formula I., by the reduction of 3,4-dimethoxyacetophenone of formula II, characterized by, that the carbonyl group of the 3,4-dimethoxyacetophenone of formula II is reduced with 1 mol of hydrogen under catalytic hydrogenation conditions. The reduction is preferably carried out by use of Raney-nickel catalyst. in a protic solvent, preferably in aqueous medium, at 25–100° C., preferably at a temperature between 50–100° C., under a pressure of 1–20 bar, preferably under a pressure between 5–10 bar.

As for Raney-nickel catalyst preferably neutral-weakly basic pH 7–9 promoted Raney-nickel is applied, in an amount of 0.05–0.5 part of mass.

The present process has a number of advantages compared to the previously known processes:

the yield is practically quantitative, the product can be isolated by filtration followed by a simple evaporation, it is of high purity, it does not require further purification, the product is in crystalline form, thus it is more stable, more easy to handle, and it can be stored better, the catalyst which has been filtered off, can be re-used in the next reduction, the use of water as solvent is very advantageous, considering both safety and economy, the technology has a good capacity factor, the reactor volume is well utilized, while the reaction time is only a few hours, waste materials, by-products are not formed.

Further details of the invention are demonstrated by the following examples, without limiting the claims to the examples.

EXAMPLE 1

Into a 10-L hydrogenation vessel, equipped with an internal coil for heating and cooling, stirrer, manometer and thermometer, 3.5 kg (19.4 mol) of 3,4-dimethoxyacetophenone are placed and to it 0.26 kg (0.074 mass part) slurry of finely-powdered Raney-nickel (pH= 8–9) promoted catalyst are washed with 1 kg of water. The reactor is filled with 3.5 kg of water, flushed with nitrogen, then with hydrogen, and under intensive stirring (revolution per minute is approx. 1420 min$^{-1}$) the mixture is reacted at 70–85° C. with hydrogen under 8–10 bar. After 7 hours the hydrogen consumption is ceased. Closing the hydrogen inlet, the reaction is post-hydrogenated for half an hour, then it is cooled. The catalyst is removed by filtration. The filtrate is concentrated in vacuo (20 torr) by a rotary evaporator, in a 40–50° C. water-bath.

The product is a yellow viscous oil, weight 3.48 kg (19.1 mol, 98.5%). Refractive index ($Na_D$, 25° C.) is 1.5385; assay by HPLC is 97.3%; water content by Karl-Fisher method is 1,2%. TLC (Kieselgel 60 $F_{254}$ benzene-EtAc 7:3 v/v) shows one spot ($R_f$=0.28, visualized by UV light and PMA).

An aliquot part is crystallized from 1.5-fold volume of diethyl ether—light petroleum (2:1, v/v) mixture. Melting point of the thus obtained white crystals is 34–35° C.

Confirmation of Structure

IR(KBr,cm$^{-1}$) ν: 3312, 3056, 3006, 2966, 2926, 2880, 2844, 1608, 1594, 1522, 1467, 1261, 1237, 1162, 1140, 1091, 1075, 1028, 861, 814.

$^1$H-NMR (200 MHz, CDCl$_3$) δ: 1.47 (3H, d, J=6.4 Hz, CH$_3$), 2.08 (1H, s, OH), 3.86 and 3.88 (total 6H, each s, CH$_3$O), 4.83 (1H, q, J=6.4 Hz, CHOH), 6.79–6.93 (3H, m, aromatic).

$^{13}$C-NMR (50 MHz, CDCl$_3$) δ: 25.05 (CH$_3$), 55.79 and 55.89 (CH$_3$O), 70.10 (ArCH), 108.65 (C-2), 110.98 (C-5), 117.48 (C-6), 138.57 (C-1), 148.28 and 149.0 (C-3, C-4).

Literature Data

CAS No: 5653-65-6

CA name: 1-(3,4-dimethoxyphenyl)-ethanol

B.p. 145–150 (4 torr), refractive index (Zhur. Obshchei Khim. 27, 2142 (1957), CA 52; 8089 g) ($Na_D$ 20° C.) 1.5440.

$^1$H-NMR (200 MHz, CDCl$_3$) δ: 1.48 (d, J=6.5 Hz), 3.86 and 0.89 (s), 4.84 (q), 6.8–6.94 (m).

$^{13}$C-NMR (Ann. 1977. 588) (50 MHz, CDCl$_3$) δ: 25.0, 55.8, 55.9, 70.1, 108.7, 111.1, 117.5, 138.6, 148.4, 149.1.

EXAMPLE 2

Into a hydrogenation vessel, equipped with an internal coil for heating and cooling, manometer and thermometer 50 g (0.278 mol) of 3,4-dimethoxy-acetophenone are placed and to it 7.5 g (0.15 mass part) slurry of finely-powdered Raney-nickel (pH=8–9) promoted catalyst are washed with 50 ml of water. The reactor is flushed with nitrogen, then with hydrogen, and is reacted at 70–85° C. with hydrogen under 8–10 bar, while agitating with a shaker. After 3.5 hours the hydrogen consumption is ceased. Closing the hydrogen inlet, the reaction is post-hydrogenated for half an hour; then it is cooled. The catalyst is removed by filtration. From the filtrate water is evaporated in vacuo (20 torr) by a rotary evaporator, in a 40–50° C. water-bath. The produc is a yellow viscoseous oil, mass: 49.6 g (0.273 mol, 98%). The quality of the product is similar to that of the product obtained in Example 1.

What is claimed is:

1. A process for the preparation of 1-(3,4-dimethoxyphenyl)ethanol of formula I

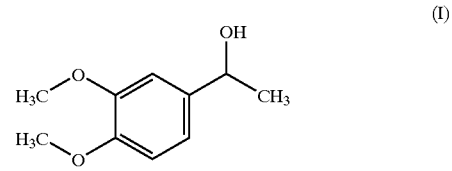

by the reduction of 3,4-dimethoxyacetophenone of formula II, wherein the carbonyl group of 3,4-dimethoxyacetophenone of formula II

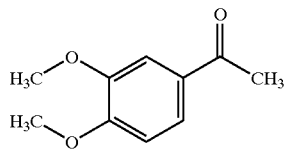

is reduced by 1 mol of hydrogen under catalytical hydrogenation conditions wherein Raney Nickel is used as catalyst under aqueous conditions.

2. Process according to claim 1, characterized by, that the reduction is carried out by using a Raney-nickel catalyst.

3. The process according to claim 1 or 2, wherein pH 7–9 promoted Raney-nickel is used as a catalyst, in an amount of 0.05–0.5 part of mass.

4. The process according to claim 1, wherein the reduction is performed at a temperature between 25–100° C.

5. The process according to claim 1, wherein the reduction is performed by using hydrogen under a pressure of 1–20 bar.

6. The process according to claim 4 wherein the temperature is between 50–100° C.

7. The process according to claim 5 wherein the pressure is 5–10 bar.

* * * * *